United States Patent [19]

Steinetz et al.

[11] Patent Number: 5,108,897
[45] Date of Patent: Apr. 28, 1992

[54] RELAXIN TESTING FOR EARLY DETECTION OF PREGNANCY IN DOGS

[75] Inventors: Bernard G. Steinetz, Franklin, N.J.; Laura T. Goldsmith, New York; George Lust, Ithaca, both of N.Y.

[73] Assignee: Cornell Research Foundation, Inc., Ithaca, N.Y.

[21] Appl. No.: 252,238

[22] Filed: Sep. 30, 1988

[51] Int. Cl.$^5$ .......................... C12Q 1/00; G01N 33/53
[52] U.S. Cl. ......................................... 435/7.9; 436/65; 436/545; 436/814; 436/817
[58] Field of Search ............... 435/7; 436/518, 520, 436/533, 540, 545, 547, 65, 804, 808, 814, 817

[56] References Cited

U.S. PATENT DOCUMENTS 4,705,748 11/1987 Sasser et al. .......................... 436/525

OTHER PUBLICATIONS

Loumaye et al., *Gynecol. Obstet. Invest.*, vol. 9 (5), pp. 262-267 (1978).
O'Byrne et al., *Journal of Clinical Endocrinology and Metabolism*, vol. 47(5), pp. 1106-1110 (1978).
Steinetz et al., *Biology of Reproduction*, vol. 37(3), pp. 719-725 (1987).
Stewart et al., *Biology of Reproduction*, vol. 32 (4), pp. 848-854 (1985).
Bodsch et al., *Fresenius Z. Analytical Chemistry*, vol. 301 (2), pp. 133-134 (1980).
Quagliarello et al., *Obstetrics and Gynecology*, vol. 53(1), pp. 62-63 (1979).
O'Byrne et al., *Proceedings of the Society for Experimental Biology and Medicine*, vol. 152, pp. 272-276 (1976).

*Primary Examiner*—Sam Rosen
*Attorney, Agent, or Firm*—Jones, Tullar & Cooper

[57] ABSTRACT

A method for determining pregnancy in a dog or cat, as well as a method for distinguishing between pseudopregnancy and actual pregnancy in a dog or cat which methods comprise measuring relaxin levels in bodily fluids or tissues which carry relaxin early in pregnancy, the presence of significant amounts of relaxin being indicative of pregnancy.

9 Claims, 6 Drawing Sheets

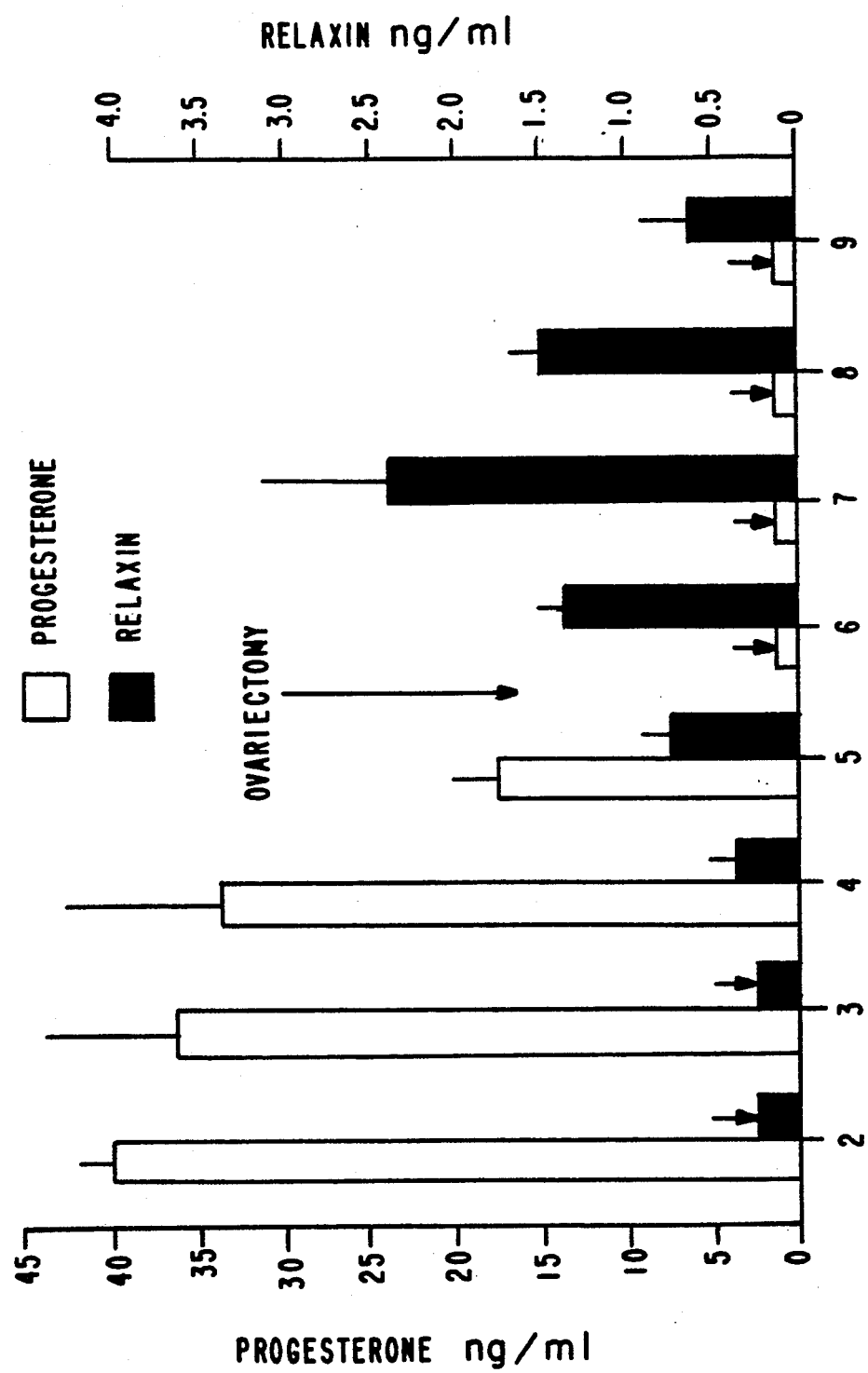

RELAXIN TESTING FOR EARLY DETECTION OF PREGNANCY IN DOGS

This work was supported in part by NIH Grant No. AN 20665. Therefore, the government has certain rights in this invention.

BACKGROUND OF THE INVENTION

Although several studies have characterized the plasma levels of progesterone and estradiol-17$\beta$ during pregnancy and lactation in the dog, there have been no studies of the polypeptide hormone, relaxin, in this species. Relaxin is a homologue of insulin that plays an important role in pregnancy maintenance and remodeling the reproductive tract in preparation for parturition in many mammalian species (please see reviews by Schwabe et al., 1978, *Recent Prog. Horm. Res.*, 34:123-199; Bryant-Greenwood, 1982, *Endocr. Rev.*, 3:62-90; MacLennan, 1983, *Clin. Reprod. Fert.* 1., 2:77-95; Weiss, 1984, *Annu. Rev. Physiol.*, 46:43-52; Kemp and Niall, 1984, *Vitam. Horm.*, 41:79-115). A product of the corpus luteum in certain species and endometrium or placenta in others, relaxin is known to inhibit uterine myometrial contractions, augment uterine growth to accommodate the growing fetuses and to increase the flexibility of the pelvic girdle and the distensibility of the uterine cervix in preparation for parturition (Schwabe et al., 1978, supra; Downing and Sherwood, 1985a, *Endocrinology*, 116:1200-1205; 1985b, *Endocrinology*, 116:1206-1214; 1985c, *Endocrinology*, 116:1215-1220). In harmony with the projected role of relaxin in mammalian pregnancy, plasma levels of this hormone increase in the latter half of pregnancy in many species (horse, cat, pig, rat, mouse, guinea pig, hamster: Sherwood et al., 1975, *Endocrinology*, 97:834-837; O'Byrne and Steinetz, 1976, *Proc. Soc. Exp. Biol. Med.*, 152:272-276; O'Byrne et al., 1976, *Endocrinology*, 99:1333-1335; Stewart and Stabenfeldt, 1981, *Biol. Reprod.*, 25:281-289; 1985, *Biol. Reprod.*, 32:848-854) and then decline just before parturition. In women and nonhuman primates, plasma relaxin is detected throughout pregnancy with no obvious peak (O'Byrne et al., 1978, *J. Clin. Endocrinol. Metab.*, 47:1106-1110; Weiss et al., 1981, *Biol. Reprod.*, 24:565-567; Castracane et al., 1983, In: Grew et al (eds.) Factors Regulating Ovarian Function, New York: Raven Press pp 415-419). Although relaxin has been shown to enhance growth of the mammary glands (Schwabe et al., 1978, supra, for older literature; Bani et al., 1985, *J. Endocrinol. Invest.*, 8:207-215; 1986, *J. Endocrinol. Invest.*, 9:153-158; Bianchi et al., 1986, *J. Endocrinol. Invest.*, 9:153-158), a role in lactation has not been proven; indeed, with the exception of one laboratory (Bryant and Chamley, 1976, *J. Reprod. Fertil.*, 46:457-459; Afele et al., 1979, *J. Reprod. Fertil.*, 56:451-457; Whitely et al., 1985, *Biol. Reprod.*, 33:705-714), most investigators have not detected relaxin in the peripheral plasma for more than 24-48 h after parturition or during the lactation period in any of the above species (Sherwood et al., 1975, *Endocrinology*, 97:834-837 & 96:1106-1113; 1980, *Endocrinology*, 107:691-698; 1981, *Biol. Reprod.*, 255:65-71; O'Byrne and Steinetz, 1976, supra; O'Byrne et al., 1976, supra; 1978, supra; Stewart and Stabenfeldt, 1981, supra; 1985, supra; Weiss et al., 1981, supra; Castracane et al., 1983, supra).

Relaxin has been shown to be present in pregnant cats using antibodies described herein (see Addiego et al, *Biol. of Reprod.*, 37:1165 Dec., 1987). The presence of pseudopregnancy in cats is described by Olson et al, *Vet Clin. N. Am. Small Anim. Prac.*, 14:927 (1984)).

BRIEF DESCRIPTION OF THE DRAWINGS

FIG. 8 shows the difference in serum relaxin levels between ovariectomized pregnant bitches and intact pregnant bitches.

DESCRIPTION OF THE INVENTION

Figure 1:
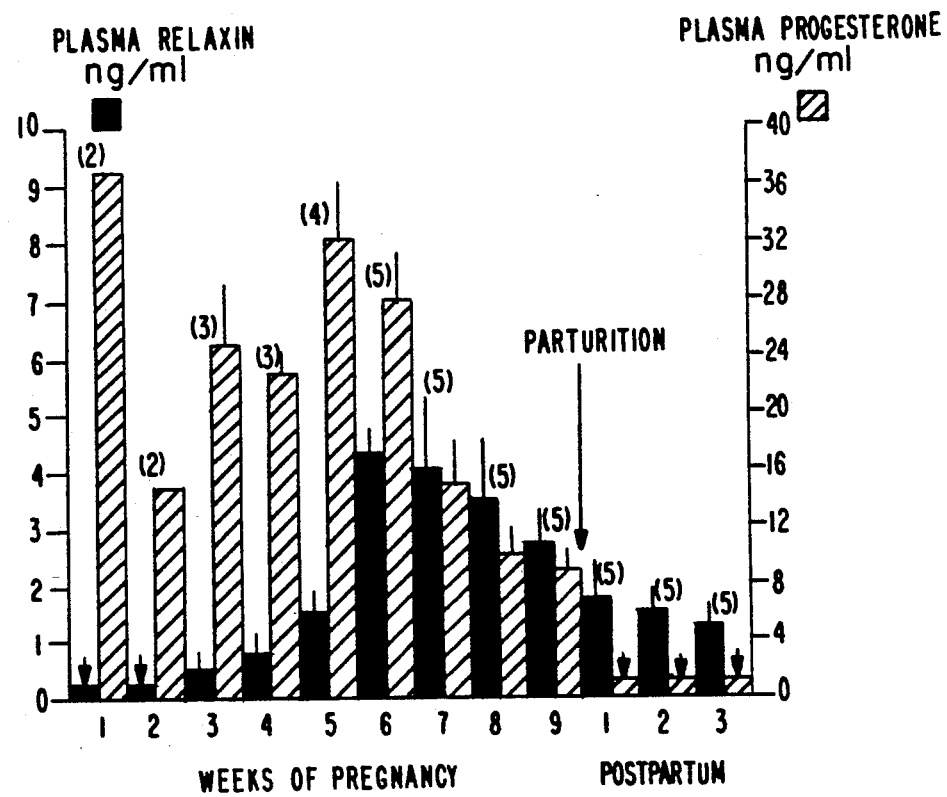
FIG. 1 shows plasma relaxin and progesterone levels in pregnant Labrador retrievers. ()=No. of dogs. ↓ = <0.18 ng/ml.

This invention relates to a method of determining pregnancy in dogs and cats and particularly to a method of distinguishing between pseudopregnancy and real pregnancy, as well as to test kits comprising marker-labeled antibodies.

Female dogs and cats upon copulation, even if they are not impregnated, frequently display all the classic signs of pregnancy, both physically and physiologically. Pet owners frequently expend considerable time and expense to assure a safe, healthy birth experience only to discover near the end of the term the bitch was not pregnant.

It has now been discovered that relaxin is a definitive marker of real pregnancy in dogs and cats but that contrary to many other biochemical changes relaxin levels do not increase in pseudopregnancy.

The method of the invention is especially useful because of the clarity of the measured results since measurable relaxin (i.e. >0.25 nanogram per ml) is not present in bodily fluids such as blood, plasma, serum, urine or milk or in tissues such as ovaries or mammary tissue except associated with actual pregnancy. Relaxin is also found in the placenta.

In the pregnant animal, levels of between about 1 and about 10 nanograms or higher of relaxin are measured in blood.

The increased relaxin level appears about three to four weeks after conception and continues through the pregnancy.

The method of assay is not unduly critical so long as the assay method is capable of determining relaxin. The presently preferred method is radioimmunoassay (liquid or solid phase) preferably, employing the double antibody method (see for example Parker "Radioimmunoassay of Biologically Active Compounds" 1976, Pentice-Hall Inc. 239 pps and "Antigen Detection to Diagnose Bacterial Infections" Vol. 1 Kohler (ed.) CRC Press Inc. Boca Raton Fla., Chapter 6, pp.61-98, 1986). Also useful are hemagglutination inhibition assays, latex agglutination assays and enzyme immunoassays (see "Antigen Detection to Diagnose Bacterial Infections" supra, Chapter 2, pp. 9-27 and Chapter 7, pp. 99-136).

Presently preferred RIA procedure. 1. One-hundred microliters of relaxin standard solutions [10 to 2500 pg relaxin in phosphate buffered saline (PBS=0.01M sodium phosphate, pH 7.0, 0.14M sodium chloride)-1% egg albumin] plus a volume of control serum or plasma (male or castrated) equivalent to that of the unknown samples were added to standard curve tabes.

2. Unknown serum or plasma samples were added to other tubes.

3. Sufficient PBS-1% egg albumin was added to each tube to bring the volume to 500 $\mu$l.

4. One-hundred microliters of [$^{125}$I] tyrosylated-relaxin in PBS-1% egg albumin (10,000 to 40,000 cpm) were added to each tube.

5. One-hundred microliters of relaxin antiserum diluted in 0.05M EDTA-PBS containing 6% male rabbit serum were added to each tube. (A 1:30,000 working dilution of the antiserum binds 30-40% of the [$^{125}$I] tyrosylated-relaxin when no competing unlabeled relaxin is present in the tube).

6. The tubes were then incubated at 4° C. for 24 hr.

7. Antibody-bound [$^{125}$I] tyrosylated-relaxin was precipitated by one of the following two methods: (a) Double antibody: Two-hundred microliters of diluted goat anti-rabbit gamma globulin (50 $\mu$l+150 $\mu$l PBS) were added to each tube. The tubes were incubated at 4° C. for an additional 24 hr and then centrifuged. (b) Polyethylene glycol: A sufficient volume of 25% w/w aqueous solution of polyethylene glycol (Carbowax 6000) at 4° C. was added to each tube to make the final concentration of the polymer 12.5% (5). The tubes were shaken and then centrifuged. Polyethylene glycol precipitates gamma globulin (5) and thus offers an economical and fast method for separating antibody-bound hormone from free hormone. However, as the volume of serum assayed is increased the number of nonspecific counts precipitated by polyethylene glycol is increased, thereby reducing the sensitivity of the assay. When relaxin levels are so low that more than 100 $\mu$l of serum or plasma are needed for a measurable response, the double-antibody procedure becomes the method of choice. This was actually the case with the samples of serum obtained from pregnant women.

In a further preferred embodiment, a matrix (M), e.g. solid or semisolid surface or permeable matrix has affixed thereto a relaxin antibody or relaxin antibody immunologically active (active against relaxin) fragment of such an antibody. This insoluble matrix is then contacted with the sample, e.g. body fluid, to bind relaxin in the sample fluid. The bound relaxin is then detected, identified and preferably quantified.

Methods suitable for detecting and quantifying bound proteins such as relaxin are generally known. Generally, after the immobilized antibody-relaxin complex has been removed from contact with the sample fluid the bound relaxin can be reacted with a detection facilitating material which reacts with a site specific to the bound relaxin and which either has a detectable group or atom measurable by an analytical technique such as a radioactive tag atom, a I.R. or U.V. light absorbing group, or which causes a visible color change; or which generates a detectable cleavage product, a leaving compound or ion, which in turn is measurable by an analytical technique.

The invention can be utilized in the form of test kits containing ingredients necessary to practice the invention; for example:

A. A kit comprising:
 1. antibody against relaxin bound to a solid matrix, and
 2. marker-labeled antibody against relaxin; and optionally
 3. where the marker is an enzyme, a substrate for that enzyme.

B. An agglutination test kit comprising:
 1. antibody against relaxin;
 2. red blood cells or latex particles sensitized with antibody against relaxin.

C. A radioummonoassay kit comprising:
 1. a relaxin standard solution;
 2. radiolabeled relaxin;
 3. first antibody against relaxin;
 4. second antibody which precipitates first antibody-bound relaxin.

EXAMPLE 1

This study was undertaken to characterize plasma relaxin levels during pregnancy and lactation in two breeds of dogs, Labrador retrievers and beagle hounds, and to compare the secretory pattern with that of progesterone, a known product of the corpus luteum in dogs. When dogs mate but fail to conceive, they may go through an extended pseudopregnancy in which steroid levels are similar to those observed in a true pregnancy (e.g. Smith and McDonald, 1974, Endocrinology, 94:404-412). The pattern of plasma relaxin and progesterone were compared in three pseudopregnant Labrador retrievers with those of the pregnant animals.

MATERIALS AND METHODS

Eight mature female Labrador retrievers and five beagle bitches of the colony at the James A. Baker Institute for Animal Health of Cornell University were used. The dogs were caged in pens with ample runs and fed a balanced diet and water ad libitum. The females were closely observed for signs of heat and placed with males when considered ready to mate. Copulation was observed on the first or second day of exposure, and blood samples were then obtained by venipuncture at approximately weekly intervals for hormone assay during the ensuing weeks of pregnancy and lactation (or pseudopregnancy in 3 dogs that mated but did not conceive). Plasma was obtained from male and anestrous female dogs for control values. All plasma samples were divided into aliquots and stored at −20° C. until assayed.

Plasma relaxin levels were determined in 400-$\mu$l samples by radioimmunoassay (RIA) using the O'Byrne and Steinetz (1976, supra) adaptation of the double antibody porcine relaxin RIA first described by Sherwood et al. (1975, supra). The method utilizes rabbit antiporcine relaxin antiserum $R_6$ at 1:30,000, [$^{125}$I]-tyrosylated porcine relaxin as radioligand, and purified porcine CM relaxin as standard. Goat anti-rabbit gamma globulin was used as precipitating antibody. The relaxin-like substance in dog plasma yielded a concentration-response curve parallel to that of the porcine standard in this homologous porcine relaxin RIA. The minimum detectable concentrations in the assays of these samples ranged from 52 to 73 pg porcine relaxin per tube. The inter and intraassay coefficients of variation were 10.71% and 5.0%, respectively. No immunoreactive relaxin was detected in plasma of male dogs or anestrous bitches. The $R_6$ antiserum has previously been shown not to cross-react with insulin or other known peptide hormones (Steinetz et al., 1981, In: Bryant-Greenwood et al (eds) Relaxin. Elsevier/North Holland pp 373-378; Loumaye et al., 1978, *Gynecol. Obstet. Invest.*, 9:262-267).

Plasma progesterone was measured in 50-µl samples by a direct specific double antibody RIA using a kit (#1024) provided by Radioassay Systems Laboratories, Inc., Carson, Calif. The method employs a rabbit antibody to 11α-hydroxyprogesterone-11α-hemisuccinate-HSA. The antiserum bound approximately 40% of the [$^{125}$I]-progesterone in the absence of unlabeled hormone. Cross-reactions of this antibody with 20α-dihydroprogesterone and deoxycorticosterone were less than 6%, and with other steroids, less than 0.5%. The minimum detectable concentration was 25 pg per tube. Inter- and intraassay coefficients of variation were 10.0% (8 assays) and 4.9% (8 replicates), respectively. The immunoreactive progesterone in dog blood yielded a concentration-response curve parallel to that of the RIA standards over the range 0.2-40 ng/ml and was additive with the standards.

Plasma estradiol-17β was measured in 25-µl samples by a direct specific double antibody RIA using a kit (#1018) provided by Radioassay Systems Laboratories, Inc. The method employs a rabbit antibody to 6-ketoestradiol-17β-6-oxime-bovine serum albumin (BSA). The antiserum bound approximately 40% of [$^{125}$I]-estradiol-17β in the absence of unlabeled hormone. Cross-reactions of this antibody with estrone, estriol, and estradiol-17α were 15, 1, and 0.7% respectively, and with androstane and pregnane derivatives, less than 0.01%. The minimum detectable concentration of estradiol was 0.25 pg/tube. Inter and intraassay coefficients of variation were 17.87% (5 assays) and 10.8% (6 replicates), respectively, in the low range of the curve, where most of the dog samples fell (10-50 pg/ml). The immunoreactive estradiol in dog plasma yielded a concentration response curve parallel to that of the estradiol standards over the range of 30-300 pg/ml and was additive with the standards.

Immunoreactive hormone concentrations were calculated after logit-log transformation of their respective standard curves. For practical reasons, the dogs were usually all bled on the same day of each week. The data for each breed were pooled according to week of gestation. Results are presented as mean concentrations of the various immunoactive hormones ± their standard errors. Statistical analyses included Student's t-test and analysis of variance, using an Apple Macintosh 512K RAM computer and the statistical package, Statworks ™, Data Metrics, Inc.

RESULTS

Figure 2:
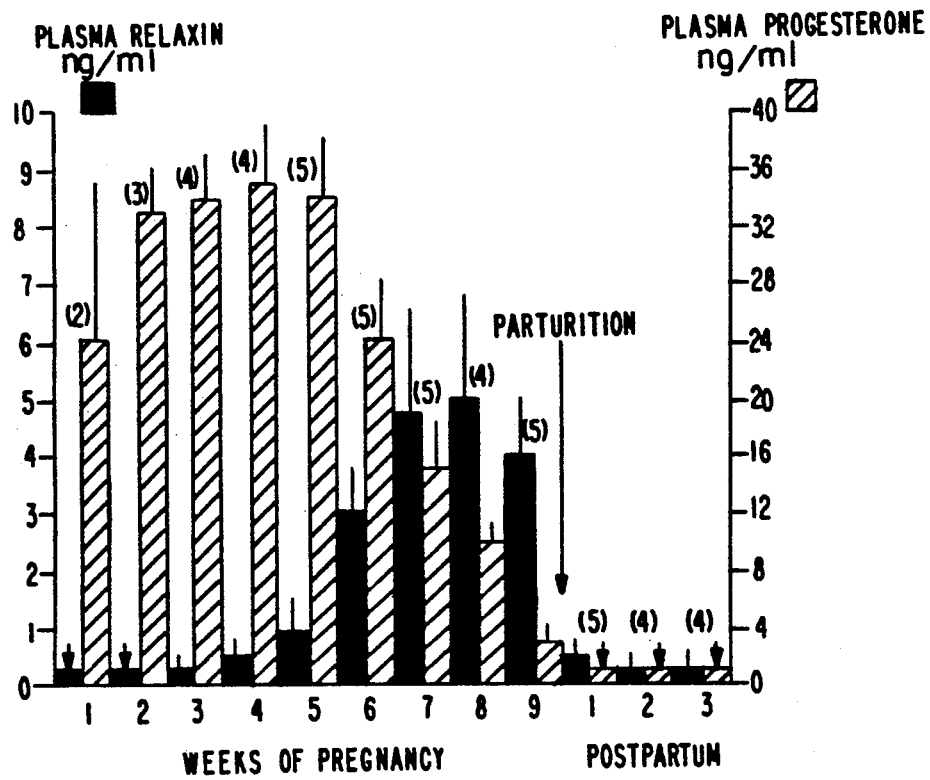
FIG. 2 shows plasma relaxin and progesterone levels in pregnant beagle hounds. ()=No. of dogs. ↓ = <0.18 ng/ml.
Figure 3:
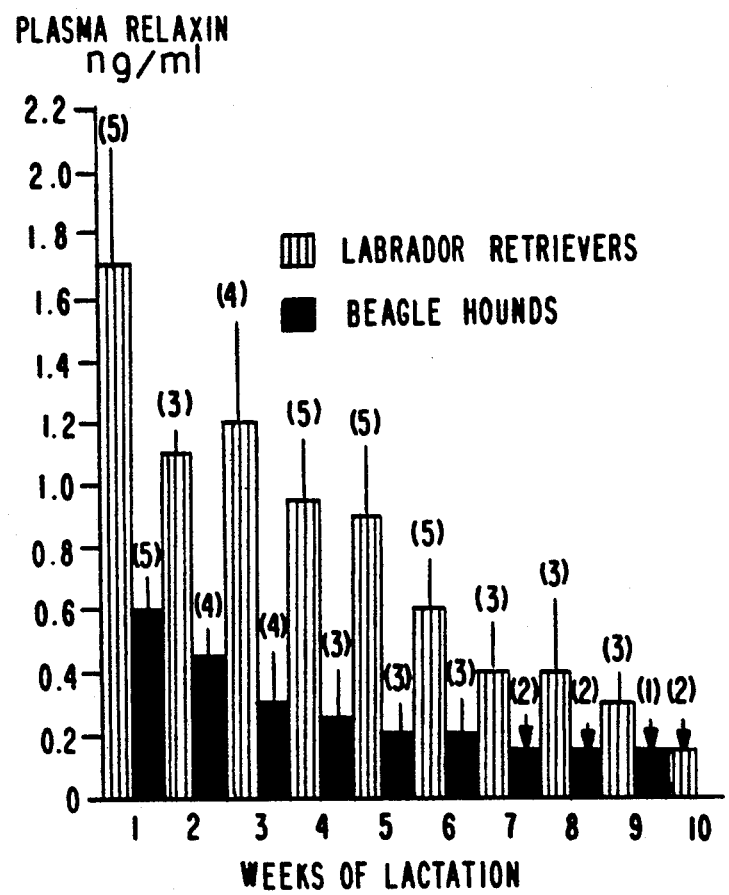
FIG. 3 shows plasma relaxin levels in lactating Labrador and beagle bitches. ()=No. of dogs. ↓ = <0.18 ng/ml.
Figure 4:
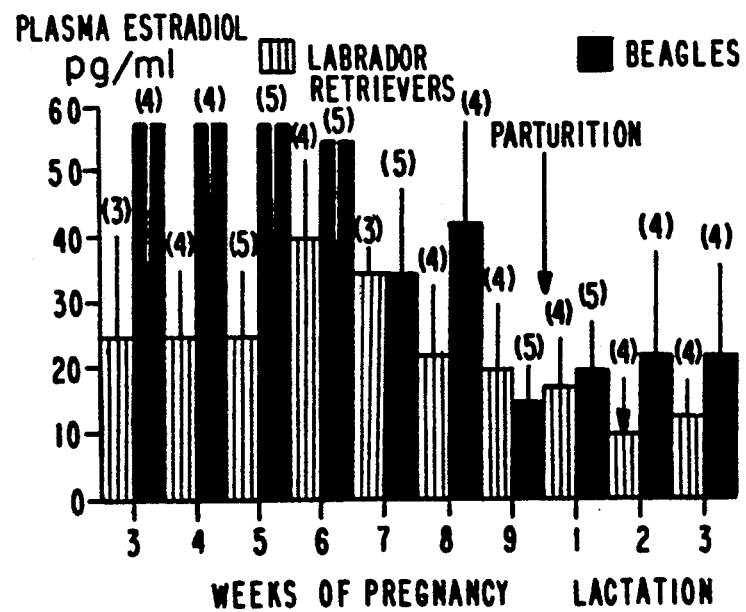
FIG. 4 shows plasma estradiol levels during pregnancy in Labrador retrievers and beagle hounds. ()=No. of dogs. ↓ = <10 pg/ml.

Immunoreactive relaxin (IR) was detected in plasma of beagle hounds and Labrador retrievers during pregnancy and lactation (FIGS. 1-3). IR was first detected in the third or forth week of gestation in both breeds, rose to a peak of 4-6 ng/ml (equivalents of porcine relaxin) 2-3 wk before whelping and declined significantly prior to that event. IR then persisted during lactation at a level of 0.5-2 ng/ml for 4-9 wk, but was significantly ($p<0.01$) higher at all time periods and persisted longer in Labradors than in beagles. The secretion of relaxin thus did not parallel that of progesterone or estradiol-17β. Progesterone was highly elevated in the first samples drawn (during the first week of pregnancy), remained high through 5 or 6 wk of gestation and then slowly declined until the time of parturition, after which it became undetectable. Estradiol levels were low throughout the latter part of pregnancy and were below 10 pg/ml during lactation in both Labradors and beagles (FIG. 4).

Figure 5:
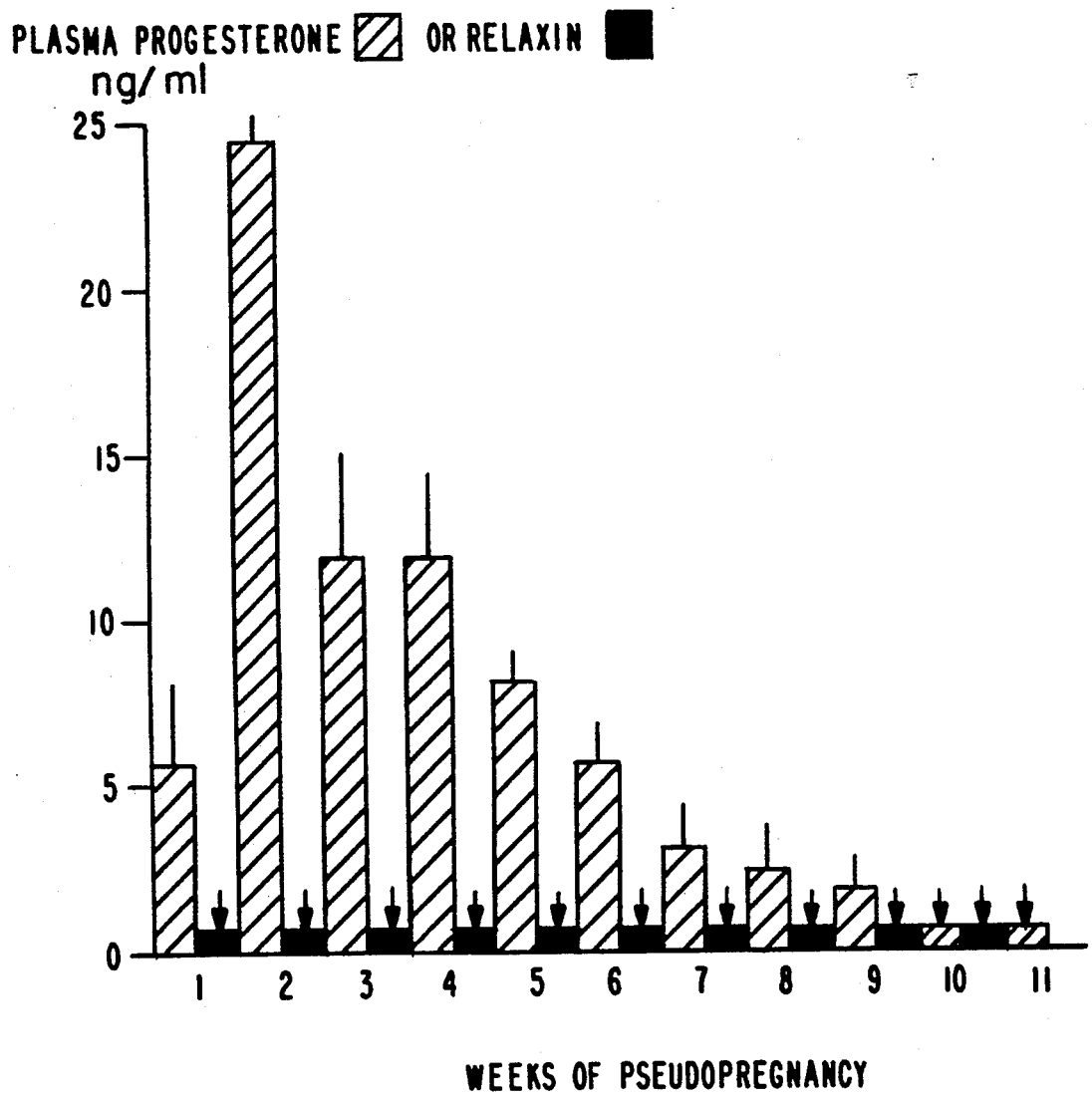
FIG. 5 shows plasma progesterone and relaxin levels in 3 pseudopregnant Labrador retrievers. ↓ = <0.18 ng/ml.

Although plasma progesterone values in pseudopregnancy were similar to those observed during pregnancy in Labrador retrievers, no relaxin could be detected during the course of pseudopregnancy in these dogs (FIG. 5).

DISCUSSION

Immunoreactive relaxin (IR) was detected in plasma of beagle and Labrador retriever bitches during pregnancy and lactation. IR was first detectable during the fourth week of pregnancy, reached its highest levels in the 6th-8th wk, and then declined prior to parturition. On the other hand, progesterone levels reached their zenith earlier and had started to decline after the 6th wk, in agreement with the studies cited in the introduction. Thus, secretion of progesterone and relaxin do not coincide during pregnancy in the dog. Furthermore, in 3 pseudopregnant Labradors, plasma progesterone levels were similar to those observed in pregnant dogs, but no IR was detectable. These data support the view that relaxin and progesterone are secreted independently of one another in the dog. Progesterone is known to be a product of the gestational corpus luteum in dogs. Further work is required to determine the source of relaxin during pregnancy in this species. The source of plasma relaxin in pregnant rats is known to be the corpus luteum (Goldsmith et al., 1981, *Endocrinology*, 109:548-552). While relaxin is not detectable by RIA in plasma of pseudopregnant rats (Goldsmith et al., 1980, 62nd Annual Meeting of the Endocrine Soc. Wash. D.C. Abstr. #369), its presence in the ovaries of such animals can be demonstrated both by the bioassay and immunoassay (Anderson et al., 1973, *J. Endocrinol.*, 59:371-372; Sherwood and Rutherford, 1981, *Endocrinology*, 108:1171-1177). In addition, both preprorelaxin mRNA and immunoreactive relaxin are detectable in rat ovaries (but not peripheral plasma) during the estrous cycle (Sherwood and Rutherford, 1981, supra; Crish et al., 1986, *Endocrinology*, 119:1222-1228).

Estradiol levels tended to be higher early in pregnancy in both breeds of dogs, and then continued at a level of 25-50 pg/ml until parturition, in agreement with numerous other studies (Jones et al., 1973, *J. Reprod. Fertil.*, 35:187-189; Nett et al., 1975, *Proc. Soc. Exp. Biol. Med.*, 148:134-139; Concannon et al., 1975, *Biol. Reprod.*, 13:112-121; Edqvist et al., 1975, *Acta Endocrinol.*, 78:554-564; Austad et al., 1976, *J. Reprod. Fertil.*, 46:129-136). None of our samples was taken as early as the estrous peak. Mean estradiol levels tended to be higher in beagles than in Labradors, but the differences were not statistically significant.

IR persisted in plasma throughout lactation, whereas progesterone and estradiol were low or not detectable. The source of relaxin in the lactating bitch is unknown, and it is also unclear whether the source of IR during lactation is the same as that during pregnancy. For reasons that are obscure, IR levels were invariably significantly higher and persisted longer in the Labrador retrievers than in the beagles during the lactation period.

EXAMPLE 2

Serum concentrations of relaxin and progesterone were measured by specific radioimmunoassays in pregnant, pseudopregnant or ovariectomized (week four-five), pregnant Labrador Retrievers. In the latter group 17α-ethyl, 19-nortestosterone was injected daily to maintain gestation. This synthetic gestagen was selected because it did not interfere with the assay in sera of endogenously secreted progesterone.

Progesterone was elevated in sera in intact pregnant or pseudopregnant bitches, but the mean progesterone concentration of pseudopregnant dogs (evaluated at 4 weeks post mating) was only 56% that of the pregnant animals. Following ovariectomy, serum progesterone fell to undetectable concentrations. Unlike progesterone, serum relaxin concentrations increased during the latter half of pregnancy in both the intact and the ovariectomized pregnant bitches, but relaxin was not detectable at any time during pseudopregnancy.

The amount of relaxin measured in the ovariectomized pregnant dogs was less ($p<0.05$) than that in intact animals, suggesting that the ovaries may have contributed to the total circulating relaxin in the intact pregnant bitches. Placental production of relaxin could account for the serum relaxin concentration following ovariectomy. It is proposed that both the ovary and placenta secrete relaxin during gestation in dogs. At parturition, the placental contribution is lost, but relaxin was still detected in the serum during lactation (Example 1). A dual source of serum relaxin in canine gestation is consistent with the lower concentrations of relaxin observed in serum of ovariectomized pregnant or lactating bitches, as compared with intact pregnant animals.

Regardless of its source, measurement of serum relaxin concentration would appear to offer a useful way of early distinction between pregnancy and pseudopregnancy in dogs.

Materials and Methods

Dogs

Eighteen mature female Labrador Retrievers were used. The dogs, which weighed between 20 and 30 kg, were caged in pens with ample runs and fed a balanced diet and water ad libitum. Females were closely observed for signs of heat and placed with males when considered ready to mate. Copulation was observed on the first or second day of exposure. Nine intact pregnant bitches were bled for relaxin and progesterone assays. One bitch had three pregnancies and four bitches were pregnant twice; thus 15 pregnancies in all were monitored. Six bitches underwent a total of eight pseudopregnancies during the study. Blood samples were drawn from the jugular vein into vacutainer tubes at approximately weekly intervals for hormone assay during the ensuing weeks of pregnancy (or pseudopregnancy/metestrus in six dogs that copulated but did not conceive). Blood was allowed to clot overnight in a refrigerator (4° C.) and serum was obtained after centrifugation and stored at −20° C. until time of assay. Serum also was obtained from three male and three anestrous female dogs for control values.

Two dogs were ovariectomized on day 35 and one on day 28 of pregnancy using standard surgical technique, anesthesia and postoperative care. These bitches were kept for an observation period of 1 week in the clinic before being returned to the kennel. Ovariectomy in pregnant dogs is known to induce abortion in 24-48 hr. if no exogenous hormonal substitution therapy is given, Sokolowski, 1971, *Lab. Am. Sci.*, 21:693-699. Accordingly, pregnancy was maintained by subcutaneous (s.c.) injection of the synthetic progestin, 17α-ethyl-19nortestosterone (ENT) in sesame oil, at a daily dose of 1 mg/kg commencing the day before surgery and continuing until day 63 of pregnancy. ENT was selected for this purpose because it does not interfere with the radioimmunoassay for progesterone, (Giannina et al, 1974, *Contraception*, 9:507-522) allowing observation of the effects of ovariectomy on serum progesterone as well as on plasma relaxin. Blood samples were collected and processed as described for the intact pregnant bitches. Although the ENT maintained pregnancy, following ovariectomy, until day 66 in one bitch, and until day 56 in two bitches, their mammary glands did not develop. Lactation did not occur in the bitch that carried to term.

Progesterone and Relaxin Assays

Serum relaxin levels were determined in 400 μl samples by radioimmunoassay using the O'Byrne and Steinetz (1976, *Proc. Soc. Exper. Biol. Med.*, 152:272-276) adaptation of the double antibody porcine relaxin radioimmunoassay first described by Sherwood et al, 1975, *Endocrinology*, 96:1106-1113. The method utilizes rabbit antiporcine relaxin antiserum $R_6$ at 1:30,000, $^{125}I$-tyrosylated porcine relaxin as radioligand and purified porcine CM relaxin as standard. Goat anti-rabbit gamma globulin was used as precipitating antibody. The relaxin-like substance in dog serum yielded a concentration-response curve parallel to that of the porcine standard in this homologous porcine relaxin radioimmunoassay.

The minimum detectable concentrations in the assays of these samples ranged from 52-73 pg porcine relaxin per tube. The inter- and intraassay coefficients of variation were 10.7% and 5.0% respectively. No immunoreactive relaxin was detected in serum of three male dogs or three anestrous bitches. The $R_6$ antiserum has previously been shown not to cross-react with insulin or other known peptide hormones (Loumaye et al, 1978, *Gynecol. Obstet. Invest.*, 9:262-267; Steinetz et al, 1981, In: Bryant-Greenwood et al (eds.) Relaxin. Elsevier-North Holland, Inc. pp. 373-378).

Serum progesterone was measured in 50 μl samples by a direct specific double antibody radioimmunoassay using a kit (#1024) provided by Radioassay Systems Laboratories, Inc. The method employs a rabbit antibody to 11a-hydroxyprogesterone-11a-hemisuccinate-HSA. The antiserum bound approximately 40% of the $^{125}I$-progesterone in the absence of unlabeled hormone. Crossreactions of this antibody with 20α-dihydroprogesterone and desoxycorticosterone were less than 6% and with other steroids less than 0.5%. The minimum detectable concentration was 25 pg per tube. Inter- and intraassay coefficients of variation were 10.0% (8 assays) and 4.9% (8 replicates) respectively. The immunoreactive progesterone in dog blood yielded a concentration-response curve parallel to that of the radioimmunoassay standards over the range 0.2-40 ng/ml and was additive with the standards.

Immunoreactive hormone concentrations were calculated after logit-log transformation of their respective standard curves. For practical reasons, the dogs were usually all bled on the same day of each week. The data were then pooled according to week of gestation. Results are presented as figures illustrating mean concentrations of the immunoactive hormones in nanograms (ng) ± standard errors of the mean.

Statistical analyses.

The concentrations of hormones in sera were converted to their natural logarithms (Ln), and a regression curve versus time (in weeks) was calculated for each dog. A predicted value for each dog was obtained from each regression curve; for relaxin at eight weeks after mating, and for progesterone at four weeks after mating. The predicted values for groups of intact (n=15) or ovariectomized pregnant (n=3) dogs, or pseudopregnant (n=8) dogs were then examined by the Student t-test. Statistical calculations were performed on an Apple Macintosh Plus computer using the statistical package Statworks TM. Significance of the difference between the mean of predicted values was set at a probability <0.05.

Results

Figure 6:
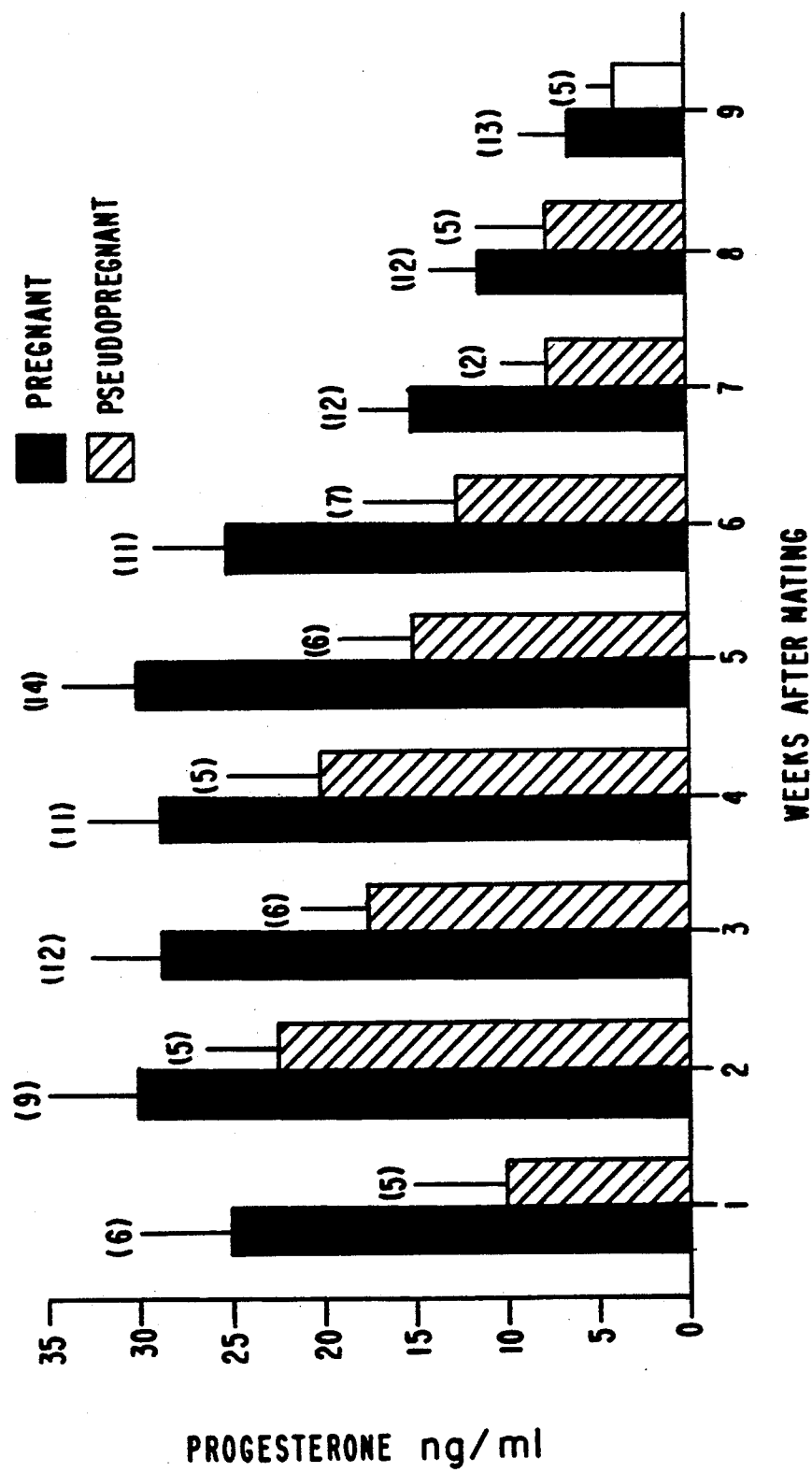
FIG. 6 presents serum progesterone levels in pregnant and pseudopregnant dogs.

Serum immunoreactive progesterone (hereafter called serum progesterone) was elevated the first week of pregnancy or pseudopregnancy, and reached its highest levels from the second through the fifth weeks (FIG. 6). The mean [and standard deviation (SD)] of the predicted values for serum progesterone was significantly higher in the pregnant than in the pseudopregnant bitches as evaluated at four weeks after mating (31.9±12.3 vs. 18.9±9.4 ng/ml: df=21: t=2.485: p<0.02).

Figure 7:
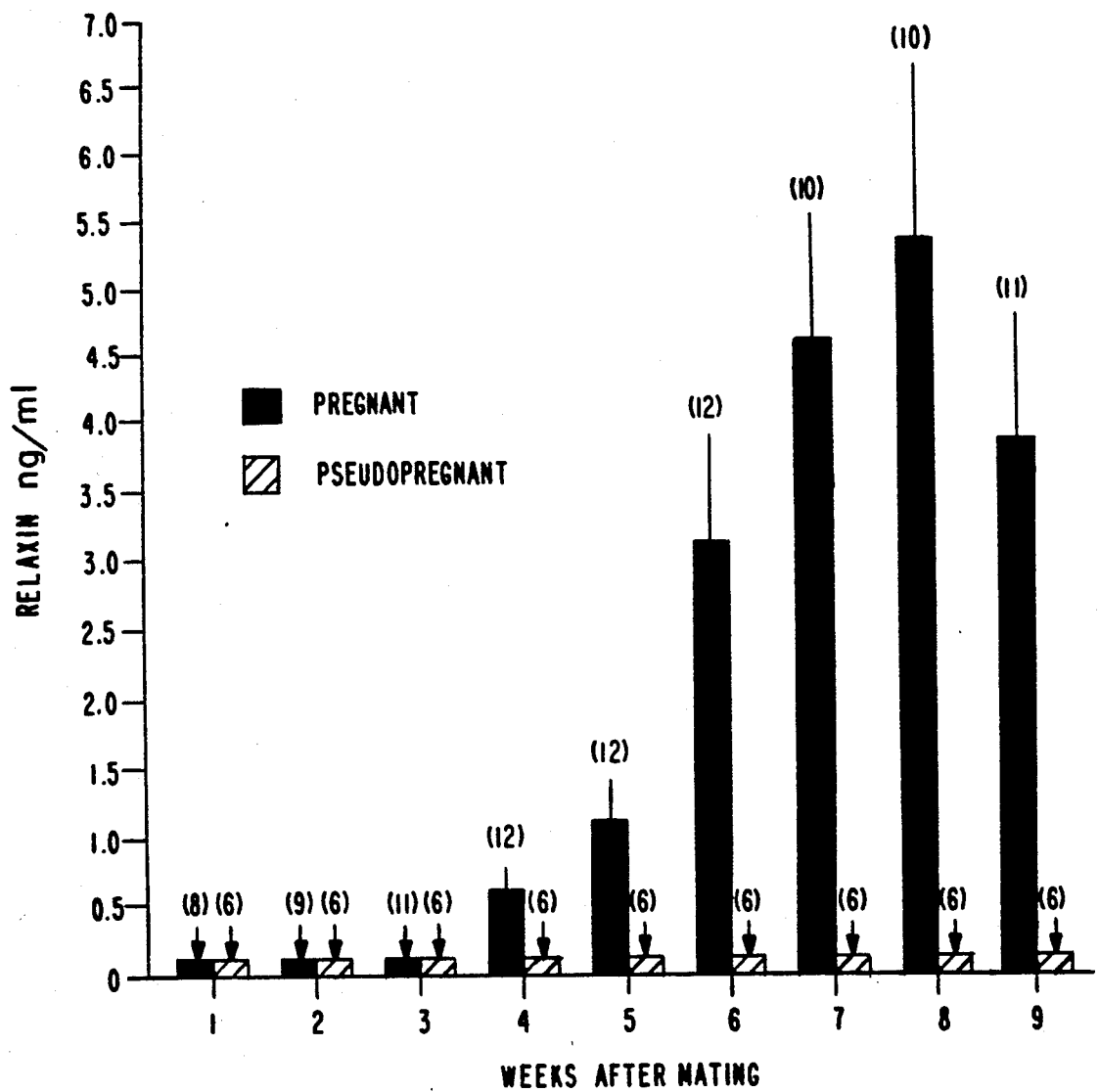
FIG. 7 presents serum relaxin levels in pregnant and pseudopregnant dogs.

Immunoreactive relaxin (hereafter called serum relaxin) was not detected before the fourth week of pregnancy, then rose to a maximum at about week six to seven, at a time when progesterone levels had started to decline (FIG. 7). Relaxin was below the limit of detectability in the serum of the pseudopregnant bitches at all times during the nine week observation period (FIG. 7).

Ovariectomy on day 28 or 35 of pregnancy resulted in a prompt decline of serum progesterone to undetectable levels (FIG. 8). Serum relaxin, however, continued to increase in the ovariectomized pregnant bitches, although the mean level of three bitches was only about 50% of that observed in a larger group (n=15) of intact pregnant dogs (FIG. 8). The differences between the predicted relaxin levels of ovariectomized and intact bitches were significantly different by t-test at the eight week sampling time (3.95±2.1 vs. 1.23±0.34 ng/ml; df=16; t=2.11; p=0.048).

Pregnancy was maintained by the ENT injections until day 56 when two of the ovariectomized bitches spontaneously aborted. One ovariectomized pregnant bitch (day 28) was maintained until day 66 when one living and 7 dead pups were recovered by cesarean section. The surviving pup was formula bottle-fed and has thrived.

Discussion

Ovariectomy of bitches on the 28th-35th day of gestation resulted in prompt loss of progesterone from the circulation, despite the fact that the pregnancies were maintained by daily injections of ENT. Sokolowski, supra, previously observed abortion to occur within 24-48 hr in ovariectomized bitches unless progesterone therapy was immediately instituted. Our data clearly show that the ovaries are the only source of serum progesterone in the canine, and are in agreement with those of Concannon et al, (1977, *Biol. Reprod.*, 16:517-526) who maintained pregnancy with medroxyprogesterone acetate in two ovariectomized Beagle bitches.

Unlike progesterone, serum relaxin continued to rise following ovariectomy in the ENT-maintained pregnant bitches although the mean relaxin concentration was less (p<0.05) in these bitches than was observed in a larger group of intact pregnant bitches. This observation might be explained by removal (via ovariectomy) of a partial contribution of ovarian relaxin to the total serum pool. Caution must be used in this interpretation since the effects of the progestin (i.e., ENT) on placental relaxin production is unknown.

Another possibility is that ovariectomy removed trophic ovarian substances that enhance relaxin secretion from other tissues. Thus, estrogen and progesterone are known to induce the endogenous formation of relaxin by uterine tissue in rabbits and guinea pigs (Hisaw et al, 1950, *Vit. Horm. VIII:* 151-178; 1944, *Endocrinology*, 34:122-134). However, the steroid-stimulated uterus does not appear to be a likely source of relaxin in the bitch, because progesterone levels were similar the first seven weeks of pregnancy and pseudopregnancy in the bitch, yet relaxin was only detectable in the former reproductive state.

Present data do not exclude absolutely the possibility that ENT, itself, may somehow partially suppress or interfere with relaxin formation. A reasonable inference to the correct interpretation derives from the observation that mammary gland enlargement did not occur in the ovariectomized, ENT-maintained bitches, although their pregnancies proceeded for eight weeks or more. This suggests that ENT did not substitute for estrogen and progesterone at least insofar as mammary gland growth is concerned.

It is not known if there is a trophic factor for relaxin synthesis or secretion in the dogs. The possibility that prolactin may be such a factor is at least suggested by the following. The initial rise in prolactin (days 25-30) coincides with the time that relaxin first appears in the circulation of the pregnant bitch, (Steinetz et al, 1987, *Biology of Reproduction* 37:719-725; DeCoster et al, 1983, *Acta Endocrinol.*, 103:473-478); both hormones reach their highest levels over the last four weeks of pregnancy; and finally, prolactin and relaxin secretion persist during the lactation interval, when levels of other potential trophic factors such as estradiol, progesterone and LH are negligible (Steinetz et al, 1987, supra; Concannon et al, 1975, *Biol. Reprod.*, 13:112-121; Smith et al, 1974, *Endocrinology*, 94:404-412). Whether or not this interpretation is correct, our data suggest that the ovary is not the only source of relaxin in serum of dogs. Furthermore they suggest that relaxin and progesterone are independently regulated and secreted in this species.

The failure in the present study to detect relaxin in serum of pseudopregnant dogs substantiates our preliminary observation and points to a fundamental difference in the regulation of the hormonal milieu of pseudopregnancy as compared with true gestation. It has been previously observed that serum levels of progesterone tended to be lower and decline earlier in metestrous than in pregnant dogs. Concannon et al (1977, *Biol. Reprod.*, 16:517-526) point to major differences in hematocrit and plasma volume between the two reproductive states, and Anderson and Simpson (the ovary and reproductive cycle of the dog (Beagle) Los Altos: Geronx, 1973, 290pps) found histological evidence of earlier regression of corpora lutea obtained from metestrous than from pregnant dogs. The latter workers also noted that the rete ovarii, which enlarges during estrus in the canine, remains enlarged during pregnancy, but decreases in size during metestrus, Smith et al, supra. None of these factors would appear to account for the absence of relaxin in sera of pseudopregnant bitches.

What is claimed is:

1. A method for determining pregnancy in a dog which comprises measuring relaxin levels in body fluids or tissues which carry relaxin during pregnancy, the presence of relaxin being indicative of pregnancy said measuring taking place early in pregnancy and before pseudopregnancy can be distinguished from real pregnancy.

2. A method of claim 1 where the levels are measured at least about four weeks after impregnation.

3. The method as in claim 1 where the relaxin is measured in blood or a relaxin-bearing blood fraction.

4. The method as in claim 3 where a level of relaxin greater than about 0.25 nanogram per ml of the blood fraction is indicative of pregnancy.

5. The method as in claim 1 where the relaxin level is determined employing a radioimmunoassay.

6. The method as in claim 1 where relaxin level is determined employing an enzyme immunoassay.

7. The method as in claim 1 where relaxin is determined employing an agglutination assay.

8. The method as in claim 1 where the body fluid or tissue is selected from the group consisting of blood, plasma, serum, urine, milk, ovary or mammary tissue and placenta.

9. A method of distinguishing between actual pregnancy and pseudopregnancy in a dog which comprises measuring relaxin levels in body fluids or tissues which carry relaxin during pregnancy, the presence of relaxin being indicative of pregnancy said measuring taking place early in pregnancy and before pseudopregnancy can be distinguished from real pregnancy.

* * * * *

UNITED STATES PATENT AND TRADEMARK OFFICE
CERTIFICATE OF CORRECTION

PATENT NO. : 5,108,897

DATED : April 28, 1992

INVENTOR(S) : STEINETZ et al.

It is certified that error appears in the above-identified patent and that said Letters Patent is hereby corrected as shown below:

On title page,
Change the assignee (item 73) to read: --New York University, New York, N.Y., assignee of Bernard J. Steinetz; University of Medicine and Dentistry of New Jersey, Newark, N.J., assignee of Laura T. Goldsmith; and Cornell Research Foundation, Inc., assignee of George Lust--

Signed and Sealed this

Eighteenth Day of October, 1994

Attest:

BRUCE LEHMAN

Attesting Officer     Commissioner of Patents and Trademarks